US011259878B2

(12) United States Patent
Hladio et al.

(10) Patent No.: US 11,259,878 B2
(45) Date of Patent: Mar. 1, 2022

(54) SYSTEMS AND METHODS FOR SURGICAL NAVIGATION WITH A TRACKER INSTRUMENT

(71) Applicant: INTELLIJOINT SURGICAL INC., Waterloo (CA)

(72) Inventors: Andre Novomir Hladio, Hamilton (CA); Kevin Morency, Guelph (CA); Alina Oprea, Waterloo (CA); Samantha McCabe, Kitchener (CA)

(73) Assignee: INTELLIJOINT SURGICAL INC., Kitchener (CA)

( * ) Notice: Subject to any disclaimer, the term of this patent is extended or adjusted under 35 U.S.C. 154(b) by 878 days.

(21) Appl. No.: 15/991,334

(22) Filed: May 29, 2018

(65) Prior Publication Data

US 2018/0338799 A1 Nov. 29, 2018

Related U.S. Application Data

(60) Provisional application No. 62/512,127, filed on May 29, 2017.

(51) Int. Cl.
*A61B 34/20* (2016.01)
*G06T 7/70* (2017.01)
(Continued)

(52) U.S. Cl.
CPC .............. *A61B 34/20* (2016.02); *A61B 5/061* (2013.01); *A61B 5/4851* (2013.01); *A61B 17/1742* (2013.01); *G06T 7/70* (2017.01); *A61B 17/155* (2013.01); *A61B 17/1746* (2013.01); *A61B 34/30* (2016.02); *A61B 2017/00725* (2013.01);
(Continued)

(58) Field of Classification Search
CPC .............. A61B 17/155; A61B 17/1742; A61B 17/1746; A61B 2017/00725; A61B 2034/2046; A61B 2034/2055; A61B 2034/2057; A61B 2034/2065; A61B 2034/2068; A61B 2090/3938; A61B 34/20; A61B 34/30; A61B 5/061; A61B 5/4851; G06T 7/70
See application file for complete search history.

(56) References Cited

U.S. PATENT DOCUMENTS

| | | | | |
|---|---|---|---|---|
| 7,043,961 | B2 * | 5/2006 | Pandey | A61B 90/36 73/1.75 |
| 2003/0187351 | A1 * | 10/2003 | Franck | A61B 90/10 600/429 |

(Continued)

*Primary Examiner* — Amanda Lauritzen Moher

(57) ABSTRACT

There is provided a surgical instrument for navigated surgeries and systems and methods using such a surgical instrument. The surgical tool comprises a tip; a tool interface, separate from the tip; and an optically trackable target. The tip is configured to probe positions in a space and identify the positions using optical information from the optically trackable target. The tool interface is configured to mate with a surgical tool such that the optical trackable target then provides optical information with which to determine positional information for the surgical tool in the space. In one example, the system provides navigational information during surgery using the surgical instrument, namely, a single integrated tracker instrument with two or more mechanical interfaces for coupling the tracker instrument with anatomical features and/or surgical tools.

21 Claims, 7 Drawing Sheets

(51) Int. Cl.
  *A61B 17/17*  (2006.01)
  *A61B 5/00*  (2006.01)
  *A61B 5/06*  (2006.01)
  *A61B 17/00*  (2006.01)
  *A61B 34/30*  (2016.01)
  *A61B 17/15*  (2006.01)
  *A61B 90/00*  (2016.01)

(52) U.S. Cl.
  CPC ............... *A61B 2034/2046* (2016.02); *A61B 2034/2055* (2016.02); *A61B 2034/2057* (2016.02); *A61B 2034/2065* (2016.02); *A61B 2034/2068* (2016.02); *A61B 2090/3983* (2016.02)

(56) References Cited

U.S. PATENT DOCUMENTS

| | | | | |
|---|---|---|---|---|
| 2005/0261697 | A1* | 11/2005 | Canonaco | A61B 17/155 |
| | | | | 606/89 |
| 2007/0016009 | A1* | 1/2007 | Lakin | A61B 34/20 |
| | | | | 600/424 |
| 2007/0038223 | A1* | 2/2007 | Marquart | A61B 34/20 |
| | | | | 606/86 R |
| 2016/0022374 | A1* | 1/2016 | Haider | A61B 17/142 |
| | | | | 606/96 |
| 2017/0143433 | A1* | 5/2017 | Fanson | G06T 7/337 |

\* cited by examiner

SYSTEMS AND METHODS FOR SURGICAL NAVIGATION WITH A TRACKER INSTRUMENT

FIELD

The present application relates to surgery systems and more particularly to systems and methods for surgical navigation with a tracker instrument.

BACKGROUND

Navigated surgical procedures may rely on identifying anatomical landmarks using the tip of a probe (e.g., for anatomical registration). Navigated surgical procedures may rely on measuring the relative pose of a surgical tool (such as an acetabular cup insertion tool or a cutting guide slot) and a patient's anatomy, and providing navigational information based on the relative pose for display to an operating surgeon, or to a robotic control system for controlling a surgical robot.

There are several modalities for surgical navigation systems, including optical (monocular), optical (stereoscopic), inertial and electromagnetic. FIG. 1 (Prior Art) illustrates an exemplary surgical navigation system 100 comprising a reference element 102 (a camera) mounted to a pelvis 104 via bone fixation hardware 106, and an instrument 108 (aka a "tracker" or "tracker instrument") comprising an optically trackable target 110 (a constellation of reflective spheres). This instrument may have probe tip 112 such as for pointing to landmarks. A computing unit, not shown, is communicatively coupled to the camera (e.g. via cable 116 or by other manners (e.g. wirelessly) and receives optical information (e.g. signals representing an image) from the camera of the optically trackable target. The computing unit processes the optical information, for example, using image processing operations, computational optimizations and spatial transformations, to provide real-time pose measurements of the instrument such as via display to a display unit (not shown). The computing unit further determines navigational information based on the pose measurements, and provides the navigational information for display or to a robotic control system. Alternatively, the computing unit may save navigational information in memory, and access this navigational information later in the procedure, for example, to generate further navigational information. The computing unit may execute a software workflow that corresponds to the surgical workflow. For example, the software workflow may comprise a series of steps.

The navigational information is spatial information that is directly or indirectly clinically relevant. For example, the navigational information may be: the position and/or orientation of an implant relative to a patient's anatomy; spatial characteristics of a patient's pre- and/or post-surgical anatomy; the position and/or orientation of a surgical tool relative to a patient's anatomy (e.g. the location of the probe tip). In many surgical procedure methods, different navigational information is important during different steps (i.e. the same surgical procedure may have at least two steps, in which different navigational information is important at that step). For example, in one step of a total hip arthroplasty, an acetabular cup is inserted. During this step, the orientation of the acetabular cup relative to patient planes is important navigational information. In another step, a femoral prosthesis is selected and implanted; during this step, the change in the patient's leg length is important navigational information.

Surgical procedures benefiting from different navigational information during different surgical steps may require a dedicated tracker for each step, or may require reconfiguration of a tracker for each step (e.g. attachment/reattachment of a tracker to different surgical tools). In either case, the cost and/or complexity of such systems is high.

SUMMARY

There is provided a surgical instrument for navigated surgeries and systems and methods using such a surgical instrument. The surgical tool comprises a tip; a tool interface, separate from the tip; and an optically trackable target. The tip is configured to probe positions in a space and identify the positions using optical information from the optically trackable target. The tool interface is configured to mate with a surgical tool such that the optical trackable target then provides optical information with which to determine positional information for the surgical tool in the space. In one example, the system provides navigational information during surgery using the surgical instrument, namely, a single integrated tracker instrument with two or more mechanical interfaces for coupling the tracker instrument with anatomical features and/or surgical tools.

In one aspect, there is a surgical instrument comprising: a tip; a tool interface, separate from the tip; and an optically trackable target; wherein the tip is configured to probe positions in a space and the optically trackable target is configured to provide optical information with which to determine the positions; and wherein the tool interface is configured to mate with a surgical tool such that the optical trackable target then provides optical information with which to determine positional information for the surgical tool in the space.

The tip and the tool interface may be located at opposite ends of the instrument. The optically trackable target may be located between the opposite ends.

The tool interface may be one of: a V-channel mounting interface; a kinematic mount; a planar feature without a magnet; and a planar feature with a magnet.

In one aspect there is provided a system to provide navigational information during a surgery comprising: an instrument comprising: a tip; a tool interface, separate from the tip; and an optically trackable target; a computing unit configured to: receive from a camera optical information of the optically trackable target; calculate a pose of the instrument based on the optical information; determine a position of the tip based on the pose of the instrument; determine first navigational information based on the position of the tip; determine a pose of the tool interface based on the pose of the instrument; determine second navigational information based on the pose of the tool interface; and provide at least one of the first and second navigational information to one or more of: a display unit for displaying to a user, computer memory for storage, and a robotic control system.

The instrument may have two opposite ends, and the tip is on one end, the tool interface is on the other end, and the optically trackable target is between the two ends.

The computing unit may be further configured to determine navigation context information; and provide the at least one of the first and second navigational information based on the navigation context information. By way of example, the computing unit may determine the navigation context information based, at least in part, on the pose of the instrument. By way of example, the computing unit may be configured to execute a software workflow comprising a series of steps, and determine the navigation context information, at least in part, based on a current step in the software workflow.

The tool interface may be one of: a V-channel mounting interface; a kinematic mount; a planar feature without a magnet; and a planar feature with a magnet. The planar feature, whether with or without a magnet, may be configured to mate with a cutting slot of a cutting guide.

The computing unit may be further configured to determine the position of the tip and/or the pose of the tool interface based at least in part on calibration data. By way of example, the calibration data may be stored in memory accessible to the computing unit, and derived from manufacturing specifications of the instrument. By way of example, the calibration data may be determined based on a calibration routine.

The first navigational information may be a limb position change and the second navigational information may be an implant alignment. The surgery may be a hip arthroplasty.

The instrument may be pre-sterilized, single-use and disposable.

The first navigational information may define at least one anatomical axis of a bone and the second navigational information may be the alignment of a bone cutting guide relative to the at least one anatomical axis. The surgery may be a knee arthroplasty.

In one aspect there is provided a system to provide leg position change information and acetabular implant alignment information during a hip arthroplasty surgery on a patient comprising: an instrument comprising a tip, a tool interface separate from the tip, and an optically trackable target; wherein the tool interface is a V-channel to mate with an axis of an acetabular implant inserter tool; and a computing unit configured to: receive optical information from a camera of the optically trackable target; calculate pose information of the instrument based on the optical information; calculate a first position of the tip when in contact with a landmark on a patient's femur, prior to arthroplasty; calculate a second position of the tip when in contact with the landmark on the patient's femur after arthroplasty; determine change in leg position information based on at least the first position and second position; calculate a pose of the tool interface when mated with an acetabular implant inserter tool during acetabular implant alignment; determine acetabular implant alignment information based on at least the pose of the tool interface; and provide leg position change information and acetabular implant alignment information to a display unit.

In one aspect there is provide a system for providing navigational information during a surgery comprising: pre-sterilized, single-use and disposable components including an instrument comprising a tip, a tool interface separate from the tip and an optically trackable target; and a tracking system comprising: a camera to generate optical information of optically trackable targets; and a computing unit configured to execute a computer-implemented workflow corresponding to a surgical workflow and provide navigational information to a display unit based on pose information derived from optical information received from the camera, the camera being communicatively coupled to the computing unit; and wherein the system for providing navigational information is free from any components requiring reprocessing for sterility. The pre-sterilized, single-use and disposable components may further include a drape configured to provide a sterile barrier around the camera, the drape further comprising an optical window to enable the camera to generate the optical information from within the sterile barrier.

In one aspect there is provided A computer implemented method to perform a navigated surgical procedure comprising: receiving, by a computing unit from a camera, first optical information of an optically trackable target, the optically trackable target comprising a component of an instrument, the instrument further comprising, separately, a tool interface and a tip, and wherein the first optical information is received when the tip is in contact with an anatomical landmark; calculating, by the computing unit, a first pose of the instrument based on the first optical information; determining, by the computing unit, a position of the tip based on the first pose of the instrument; determining, by the computing unit, first navigational information based on the position of the tip; receiving, by the computing unit, from the camera, second optical information of the optically trackable target when the instrument is coupled to a surgical tool via the tool interface; calculating, by the computing unit, a second pose of the instrument based on the second optical information; determining, by the computing unit, a pose of the tool interface based on the second pose of the instrument; determining, by the computing unit, second navigational information based on the pose of the tool interface; and providing, by the computing unit, to a display screen the first and/or second navigational information.

In one aspect there is provided A system to provide navigational information during a surgery comprising: an instrument comprising: a tip; a tool interface, separate from the tip; and an optically trackable target; a computing unit configured to: receive from a camera optical information of the optically trackable target; calculate a pose of the instrument based on the optical information; determine navigation context information based on the pose of the instrument; and responsive to the navigation context information, perform one of: A) determine a position of the tip based on the pose of the instrument; determine first navigational information based on the position of the tip; and provide the first navigational information to one or more of: a display unit for displaying to a user, computer memory for storage, and a robotic control system; and B) determine a pose of the tool interface based on the pose of the instrument; determine second navigational information based on the pose of the tool interface; and provide second navigational information to one or more of: a display unit for displaying to a user, computer memory for storage, and a robotic control system.

These and other aspects including related computer implemented method and/or computer readable media aspects will be apparent to those of ordinary skill in the art.

DETAILED DESCRIPTION

Figure 1:
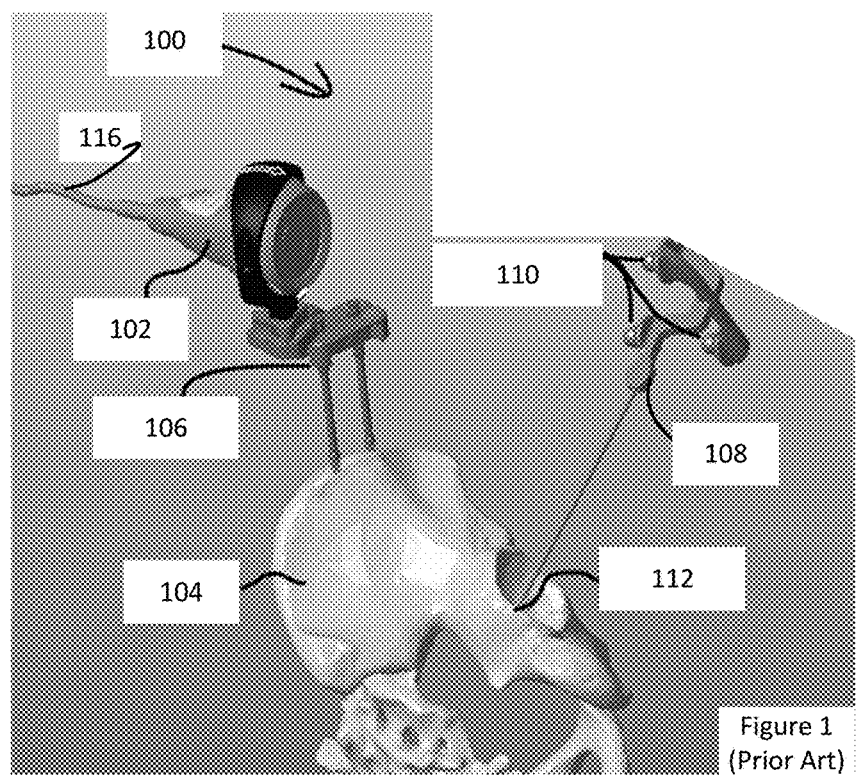
FIG. 1 is an annotated CAD illustration of components of a surgical navigational system according to the prior art.
Figure 2:
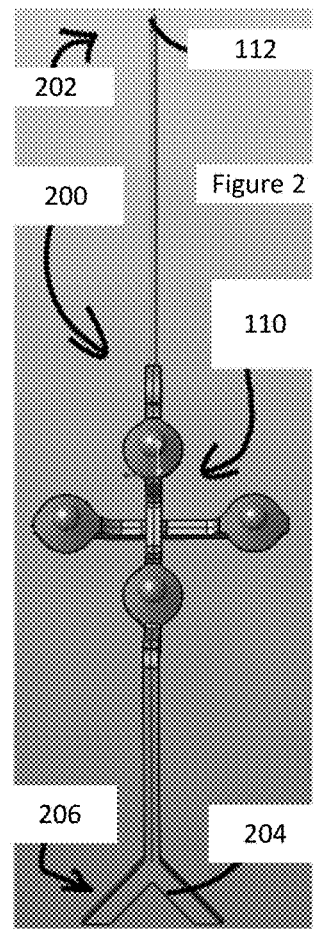
FIG. 2 is an annotated CAD illustration of a tracker instrument in accordance with an example having a V-Channel mount as one mechanical interface.

A system for providing navigational information during surgery may provide a single integrated tracker instrument with two or more mechanical interfaces for coupling the tracker instrument with anatomical features and/or surgical tools. For example, as shown in FIG. 2, a tracker instrument 200 has one mechanical interface that is a probe tip 112 similar to FIG. 1 at a first end 202 used for contacting points in space, such as anatomical landmarks, and another mechanical interface that is a tool interface. In the present example the tool interface is a V-channel 204 (e.g. a V-channel mounting interface) at a second end 206 for coupling to the main shaft of a surgical tool (not shown), such as an acetabular cup inserter used in hip arthroplasty. The tracker instrument provides an optically trackable target 110 similar to FIG. 1 in the form of a pattern of reflective spheres. The tracker instrument is a rigid body, meaning that under expected forces during use, storage or processing, the tracker instrument does not deflect mechanically. That is, it does not deflect sufficiently that the trackable target remains accurate for tracking relative to the two or more interfaces.

The tracker instrument 200 as shown in FIG. 2 may have mechanical interfaces at opposite ends with the interfaces pointing approximately 180° (plus or minus 25°) away from each other. For example, the probe tip 112 may be at a first end 202 of the tracker instrument 200, and a V-channel tool interface 204 may be at a second end 206 of the tracker instrument 200. The optically trackable target may be located between both ends. The advantage of having mechanical interfaces at opposite ends of the tracker instrument is that there is a lower likelihood that the other interface will interfere with the interface being used for coupling.

Figure 3:
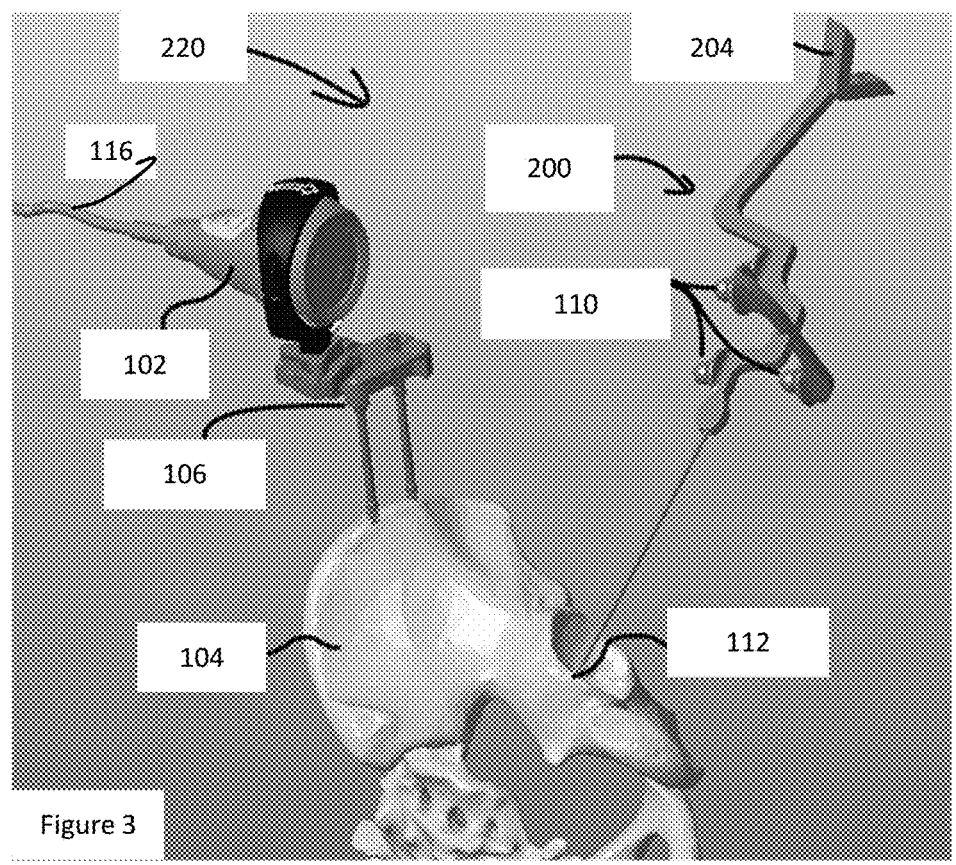
FIG. 3 is an annotated CAD illustration of components of a surgical navigation system including a tracker instrument in accordance with FIG. 2.

FIG. 3 is an illustration of components of a surgical navigation system 220 including a tracker instrument 200 in accordance with FIG. 2. A computing unit (not shown) may determine the pose (in up to 6 degrees of freedom) of the two or more mechanical interfaces by receiving tracking signals of the tracker instrument, calculating pose information of the tracker instrument based on the tracking signals, and determining the pose of the two or more mechanical interfaces based on the pose information. The computing unit may access calibration data defining the positional relationship between the trackable element of the tracker instrument and the respective mechanical interfaces to determine the mechanical interfaces' respective pose(s). These poses may be computed simultaneously or successively.

In the context of an optical localization system, the computing unit may determine the pose (in up to 6 degrees of freedom) of the two or more mechanical interfaces by receiving optical information of the optically trackable target of the tracker instrument from a camera, calculating pose information of the tracker instrument based on the optical information, and determine the pose of the two or more mechanical interfaces based on the pose information. The computing unit may access calibration data defining the positional relationship between the optically trackable target and the mechanical interfaces to determine the mechanical interfaces' respective pose(s).

Calibration data defines the positional relationship between the trackable element (e.g. the optically trackable target of an optical localization system, or an electromagnetic probe of an electromagnetic localization system) and the mechanical interfaces. The calibration data may be pre-loaded onto memory of the computing unit based on the manufacturing specifications of the tracker instrument (i.e. each tracker instrument is consistently manufactured). Alternatively, a calibration routine may be required before use, in which calibration pose data is received by a computing unit, and calibration computations are performed. For example, to determine calibration data of the tip of a probe, the tracker instrument may be pivoted about the tip, while the computing unit receives tracking signals, determines calibration pose data representing various poses during the pivoting, and computes calibration data by executing a center-of-rotation calculation based on calibration pose data.

The same tracker instrument may be used for spatial measurements of two or more features (e.g. an anatomical landmark and a surgical tool). The computing unit may determine navigation context information that represents usage of the tracker instrument at a given point during the surgery. The navigation context information identifies which mechanical interface is relevant at that moment. For example, with reference to the tracker instrument of FIG. 2 when probing anatomical landmarks, it is the probe tip that is relevant, while the tool interface (e.g. V-channel) is not relevant. The navigation context information indicates which mechanical interface is relevant at a given moment. The navigation context information may be determined in part by the pose of the tracker instrument. If the tracker instrument is oriented with the probe tip pointing downwards (and consequently the V-channel pointing upwards), the computing unit may implement a heuristic to determine that the probe tip is the currently active mechanical interface (the heuristic being based on the fact that it is unfeasible to have the V-channel pointing upwards during use).

If the computing unit is executing a software workflow, the navigation context information may be determined by the computing unit based on what step is being executed within the workflow. For example, when the current step of the software workflow corresponds to a surgical step involving the alignment of a surgical tool, the navigation context information would identify the V-channel (as opposed to the probe tip) as the relevant mechanical interface.

The computing unit may use the navigation context information to determine what to do with the navigational information. For example, certain navigational information may be stored in memory of the computing unit, while other navigational information may be provided to a display unit for display to a user. The navigation context information defines the behaviour of the computing unit with regard to how the navigational information is provided.

Figure 4:
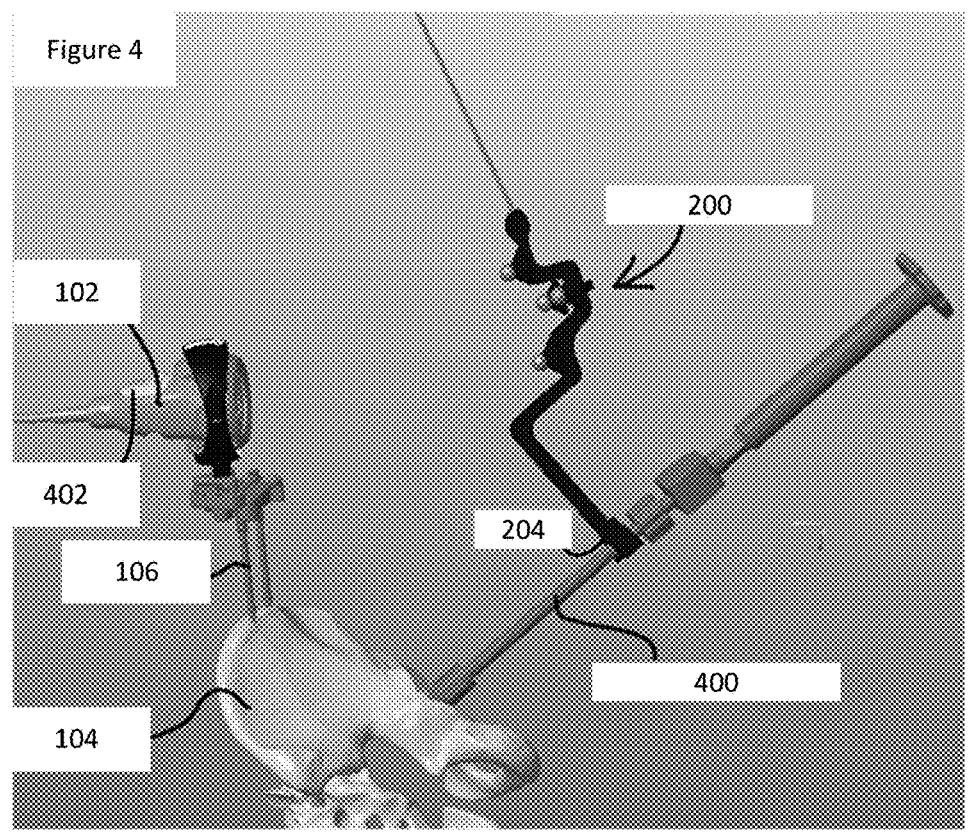
FIG. 4 is an annotated CAD illustration of the surgical navigation system of FIG. 3 with the tracker instrument coupled to an acetabular inserter.

The surgical localization system 220 comprising a tracker instrument 200 may be used by a surgeon performing total hip arthroplasty in accordance with the following exemplary method:

- A reference element of the localization system is attached to the patient's pelvis, the reference element being rigidly coupled to the pelvis, the localization system being configured to measure relative pose between the tracker instrument and the reference element (e.g. the reference element may be a camera attached to the pelvis as shown in FIG. 3).
- The patient's pelvis may be registered to the localization system by performing an anatomical registration method including contacting multiple prescribed anatomical landmarks on the pelvis using the probe tip of the tracker instrument. A computing unit of the localization system determines the position of the tip of the tracker instrument when in contact with each respective landmark, and performs registration computations to determine the registration between the reference element and the patient's pelvis.
- The hip joint is exposed.
- Prior to dislocation of the femoral head, the baseline (i.e. prior to arthroplasty) position of a landmark on the femur is determined by the computing unit when the surgeon contacts the landmark with the probe tip of the tracker instrument.
- After dislocation and acetabular preparation, the acetabular cup is coupled to an acetabular cup inserter for insertion into the prepared acetabulum.
- The surgeon couples the tracker instrument to the acetabular inserter 400 (as illustrated in FIG. 4) so that the V-channel is axially aligned with the axis of the acetabular inserter. When coupled, the computing unit of the localization system determines the orientation of the acetabular cup and provides this information to a display unit; the surgeon views the display unit and uses the information to adjust, select and/or fine tune the orientation of the acetabular cup prior to impacting it in place.
- The surgeon prepares the femur and reduces the prosthetic joint.
- The post-reduction (i.e. after arthroplasty) position of the landmark on the femur is determined by the computing unit when the surgeon contacts the landmark with the probe tip of the tracker instrument. The computing unit further determines change in leg position based on the spatial difference between pre-dislocation and post-reduction femur landmark positions.

In general, the surgeon (or any other user) may invoke the computing unit to receive tracking data (e.g. from reference element 102) when the probe (or any mechanical interface) is coupled to its respective object (e.g. anatomical landmark, surgical tool), via button presses, voice commands, foot pedals, etc. Reference element 102 may comprise one or more buttons 402.

Figure 5:
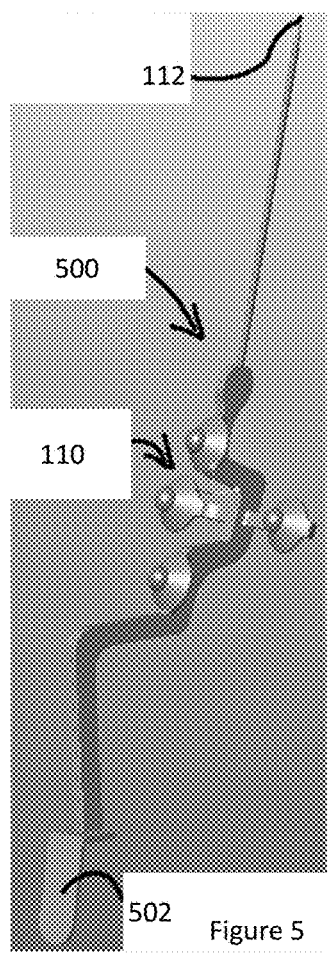
FIG. 5 is an annotated CAD illustration of a tracker instrument in accordance with an example having a planar feature as one mechanical interface.

The mechanical interfaces of the tracker instrument depend on the type of surgery, including the type of existing surgical tools to which the tracker instrument must interface to facilitate clinically relevant navigational information. A V-channel is well suited for measuring orientation of an axis. In total knee arthroplasty, navigational information about the alignment of planes is important, and knee instrumentation provides planar cutting slots that guide planar bone cuts by an oscillating saw. A tracker instrument 500, as shown in FIG. 5, provides two mechanical interfaces: a probe tip 112 and, separately, a planar feature 502 comprising the tool interface. The planar feature comprises at least one planar surface and in the present example, two opposing planar surfaces, for example, to interface with a cut slot of a knee cutting jig (not shown) used for TKA. The tool interface may include a magnet (not shown) configured to engage the planar feature with a portion of a tool. For example, when the planar feature is engaged with the (ferrous) cut slot, a magnetic force keeps the tool and slot engaged without the need for a user to hold them together. Furthermore, as the planar feature may not be sized for a perfect fit within the slot, the magnetic force may ensure that a plane of the planar feature is fully seated on the desired surface of the cut slot.

Figure 6:
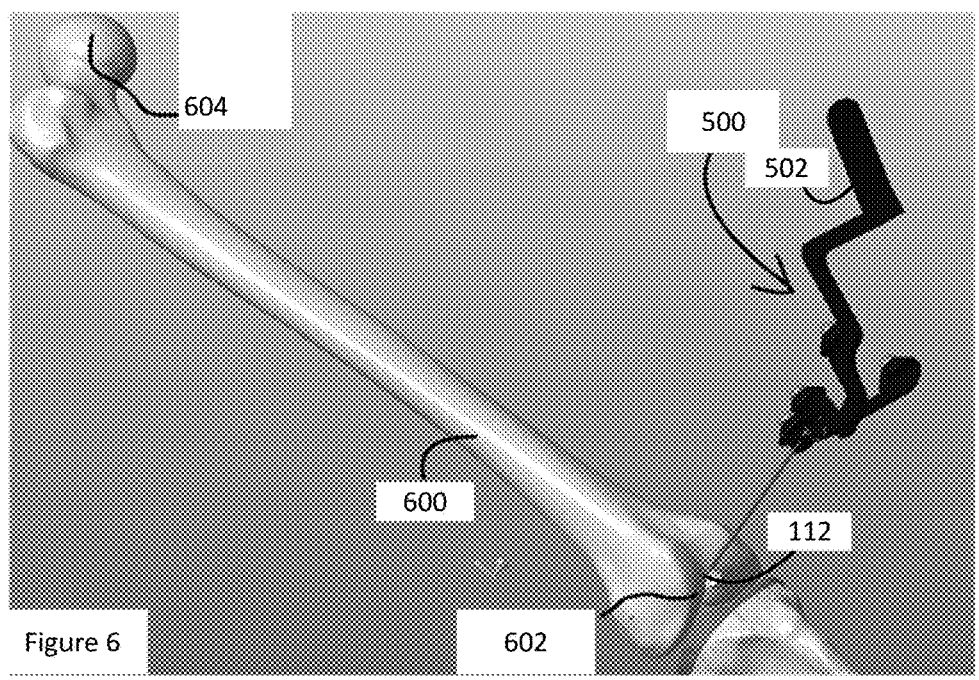
FIG. 6 is an annotated CAD illustration of the tracker instrument of FIG. 5 coupled to a femur to point to an anatomical landmark thereon, for example, to perform a femur registration.
Figure 7:
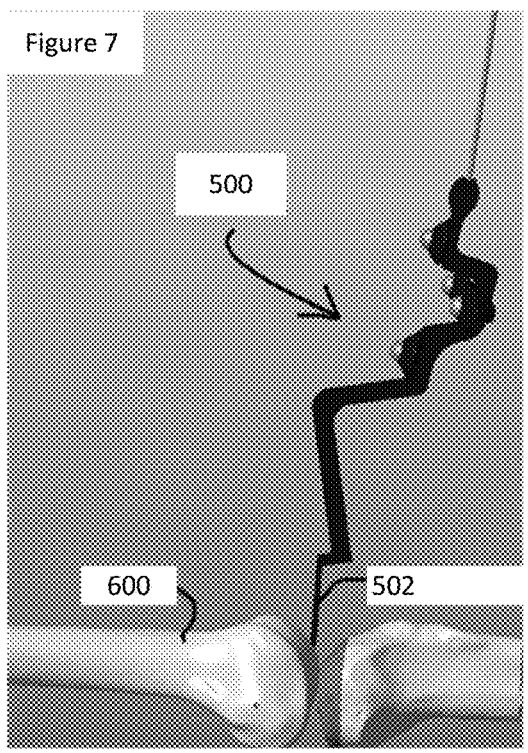
FIG. 7 is an annotated CAD illustration showing the planar feature of the tracker instrument of FIG. 5 in an alignment with the femur for example for a femur cut.

A surgical localization system such as system 220 comprising such a tracker instrument 500 may be used by a surgeon performing total knee arthroplasty in accordance with the following exemplary method:

- A reference element of the localization system is attached to the patient's femur, the reference element being rigidly coupled to the femur, the localization system being configured to measure relative pose between the tracker instrument and the reference element (e.g. the reference element may be another tracker rigidly fixed to the femur).
- The knee joint is exposed.
- The patient's femur may be registered to the localization system by performing an anatomical registration method defining at least one anatomical axis including contacting multiple prescribed anatomical landmarks on the femur 600 using the probe tip 112 of the tracker instrument 500 (as illustrated in FIG. 6, where the probe tip is shown contacting the femoral epicondyle 602) and/or articulating the hip joint about its hip center of rotation 604 while the reference element is tracked by the localization system. A computing unit of the localization system performs registration computations based on probe tip and/or center of rotation data to determine the registration between the reference element and the patient's femur. The femur registration may be navigational information that is saved in computer memory.
- The patient's tibia may be registered to the localization system by performing an anatomical registration method defining at least one anatomical axis including contacting multiple prescribed anatomical landmarks on the femur using the probe tip of the tracker instrument. A computing unit of the localization system performs registration computations based on probe tip data to determine the registration between the reference element and the patient's tibia. The tibia registration may be navigational information that is saved in computer memory.
- The planar feature of the tracker instrument is coupled with the cutting slot of a femoral cutting jig. FIG. 7 is a CAD illustration showing the planar feature in an alignment with the femur (note: the cutting jig is not shown for clarity).
- The cutting jig is fixed into alignment with the femur based on navigational information provided on a display comprising the orientation of the cutting plane relative to the femur as defined by the femur registration, the navigational information based on the calculated pose of the planar feature.
- The femur is cut, and the cutting jig is removed.

The planar feature of the tracker instrument is coupled with the cutting slot of a tibial cutting jig.

The cutting jig is fixed into alignment with the tibia based on navigational information provided on a display comprising the orientation of the cutting plane relative to the tibia as defined by the tibia registration, the navigational information based on the calculated pose of the planar feature.

The tibia is cut, and the cutting jig is removed.

The tibia and femur are fitted with implants, and the joint is reduced.

Figure 8:
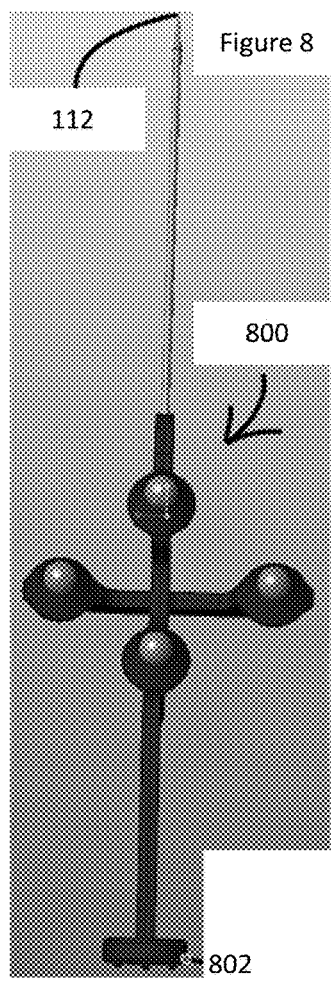
FIG. 8 is an annotated CAD illustration of a tracker instrument in accordance with an example having a kinematic mount as one mechanical interface.
Figure 9:
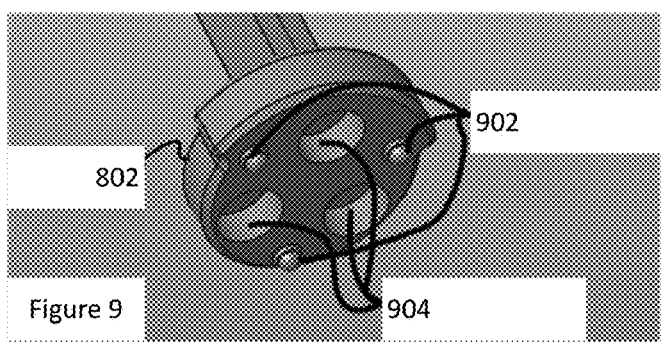
FIG. 9 is an annotated CAD illustration of details of the kinematic mount of FIG. 8.

FIG. 8 is an annotated CAD illustration of a tracker instrument 800, in which one mechanical interface is a kinematic mount 802 that is repeatable in 6 degrees of freedom (i.e. when coupled to a mating kinematic mount, the position and orientation of the tracker instrument is fully constrained). The other mechanical interface is the tip of a probe 112. FIG. 9 is an annotated CAD illustration showing details of exemplary kinematic mount 802, in which three partly spherical features 902 and three magnet locations 904 are shown (note: magnets not shown). A mating kinematic mount has three slots and three magnets corresponding to the kinematic mount shown, such that the magnets impart a holding force keeping both sides of the mount engaged with the three partly spherical features contacting the three slots.

Figure 10:
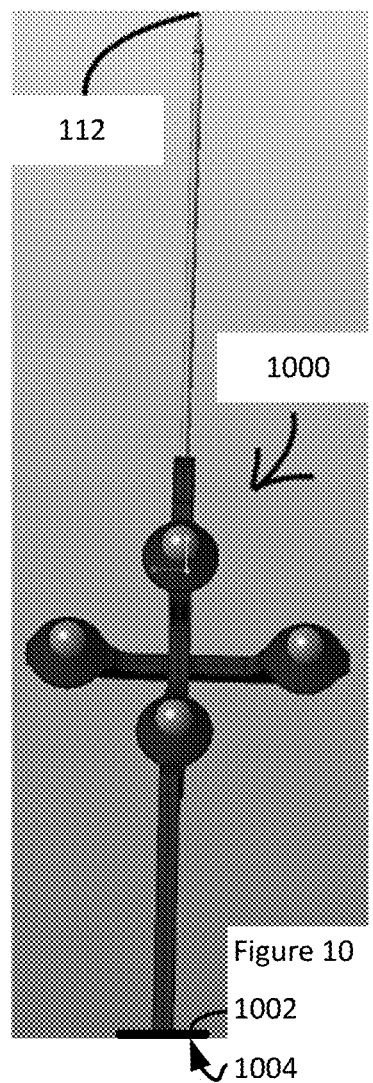
FIG. 10 is an annotated CAD illustration of a tracker instrument in accordance with an example having a planar feature, cylindrical in shape, as one mechanical interface.
Figure 11:
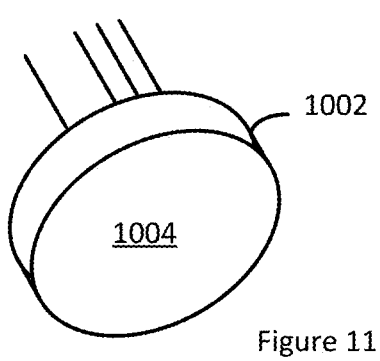
FIG. 11 is an illustration showing an enlarged perspective view from an end of the tracker instrument of FIG. 9 showing the planar feature.

FIG. 10 is an annotated CAD illustration of a tracker instrument 1000, in which one mechanical interface is a planar feature 1002, having a planar surface 1004 cylindrical in shape, which is oriented transverse to the longitudinal axis of the tracker instrument. FIG. 11 shows a partial enlarged perspective view of tracker instrument 1000 from the end having the planar feature 1002, similar to the orientation of FIG. 9 showing the details of the kinematic mount 802. Planar feature 1002 may also be or include a magnetic base so that the instrument may be magnetically attached to an instrument, etc. The magnetic base may be the entire aspect of the planar feature or there may be a magnet positioned in a center thereof.

Determining calibration data for a tracker instrument 200 having a probe tip is described earlier herein where one method describes receiving previously stored calibration data and a second method describes generating such data by pivoting the instrument about the probe tip during a calibration routine. In a similar manner, calibration data may be received for a tracker instrument having a planar feature. There may be an analogous calibration routine by which to determine calibration data of the planar feature. For example, a user may "paint" a flat surface with the planar feature.

The complexity of a system for performing a navigated surgical procedure comprising a tracker instrument as described herein may be greatly reduced. For example, the number of components required to perform surgical navigation may be reduced to: one tracker instrument; one tracking system (comprising a computing unit in communication with a tracking sensor such as a camera); and one reference element. Additionally, system components may have a simplified use, since the system may require fewer steps for assembly and interfacing (e.g. no need for dedicated adaptors).

In particular, the usage of the components within the sterile field may be simplified (i.e. the reference element and the tracker instrument). In one implementation, the tracker instrument is pre-sterilized and single-use (disposable). Tracker instruments may be packaged in multiple layers of protective packaging to ensure sterility, shelf life and physical integrity. A new tracker instrument may be used for each surgical procedure, and the tracker instrument not require any pre-operative assembly, such as attachment of reflective spheres onto a reusable tracker.

Hospital reprocessing/sterilization (e.g. autoclaving) is costly and introduces logistical complexities when multiple surgical procedures are occurring in a single day, since there is limited time to reprocess tools/instruments/equipment. Additionally, when new equipment is brought into the hospital, it must be brought in before surgery, to allow for ample time for reprocessing, which typically occurs overnight. Eliminating the need for hospital reprocessing is desirable. In one implementation, the navigation system described herein does not require the reprocessing of any components:

the tracker instrument is pre-sterilized, single-use and disposable, the reference element is either pre-sterilized, single-use and disposable or is reusable and enclosed within a sterile barrier that is itself a pre-sterilized, single-use and disposable (such as a camera drape providing a clear window for transmission of optical signals, where the reference element is a reusable camera), the reference element fixation components (e.g. bone screws, camera clamp) are pre-sterilized single-use and disposable.

The elimination of the need for hospital reprocessing is enabled by the reduction in number and simplification of system components within the sterile field. Without the reduction in number of sterile components, disposal would be prohibitively costly and raise significant environmental concerns. Many hospitals have strict disposal and waste policies, such that only a small quantity of waste may be tolerated per procedure. Therefore, a requirement for a navigation system based on pre-sterilized, single-use and disposable components (instead of hospital-based reprocessing) is low waste generation.

Figure 12:
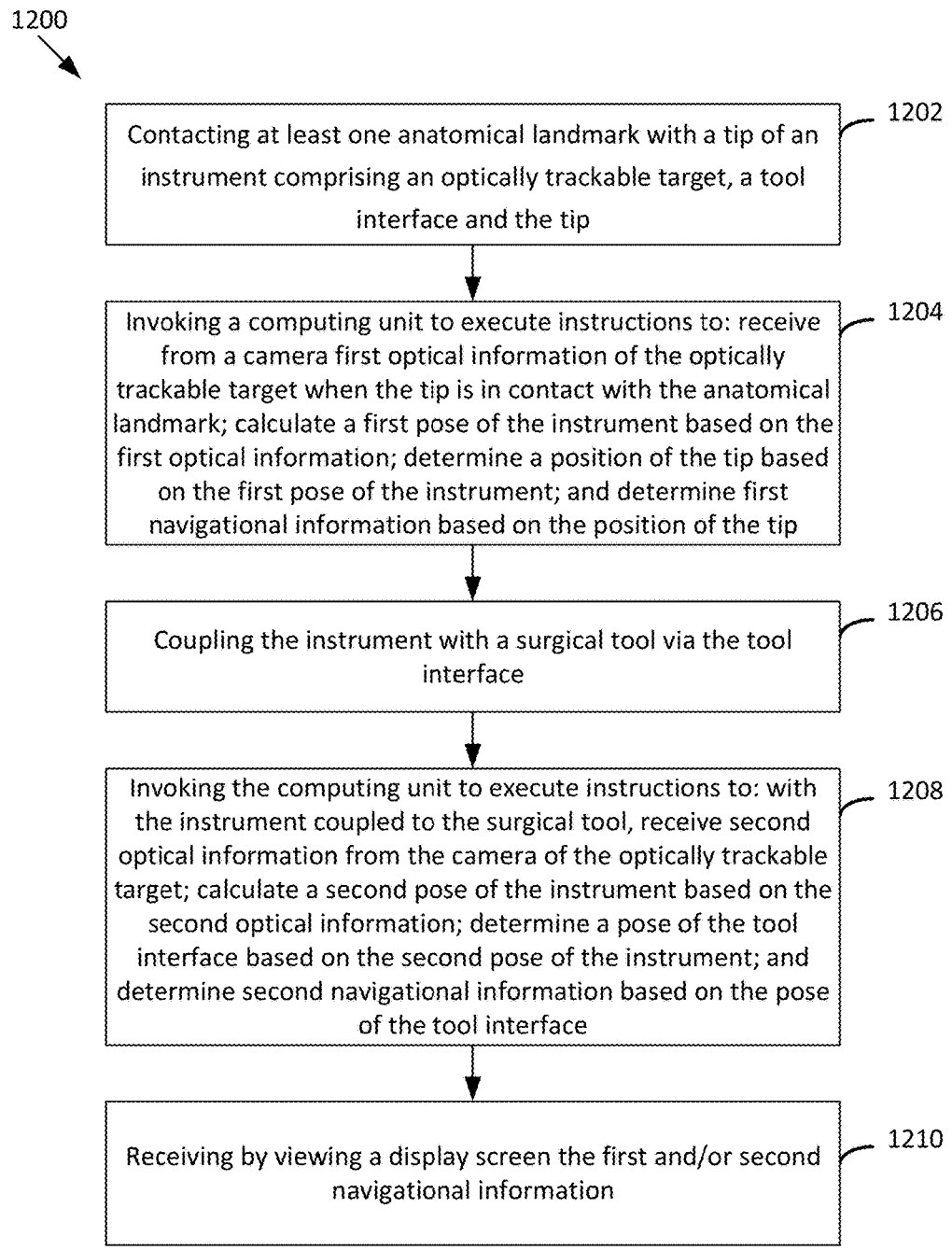
FIG. 12 is a flowchart showing a method to perform a navigated surgical procedure according to an example.

FIG. 12 is a flowchart illustrating a method 1200 to perform a navigated surgical procedure. At step 1202, the method comprises contacting at least one anatomical landmark with a tip of an instrument comprising an optically trackable target, a tool interface and the tip. At step 1204, a computing unit is invoked to execute instructions to: receive from a camera first optical information of the optically trackable target when the tip is in contact with the anatomical landmark; calculate a first pose of the instrument based on the first optical information; determine a position of the tip based on the first pose of the instrument; and determine first navigational information based on the position of the tip. At step 1206, the method 1200 comprises coupling the instrument with a surgical tool via the tool interface.

At step 1208, the method 1200 comprises invoking the computing unit to execute instructions to: with the instrument coupled to the surgical tool, receive second optical information from the camera of the optically trackable target; calculate a second pose of the instrument based on the second optical information; determine a pose of the tool interface based on the second pose of the instrument; and determine second navigational information based on the pose of the tool interface. The method 1200 comprises, at step 1210, receiving by viewing a display screen the first and/or second navigational information. The first and/or second navigational information may be provided to the display screen by the computing unit based on navigation context information. The computing unit may determine the navigation context information, for example, at least in part based on a pose of the tool interface and/or a pose of the tip.

The method 1200 may further comprise a step (not shown) of adjusting or confirming spatial attributes related to the surgical procedure based on the received navigational information.

Figure 13:
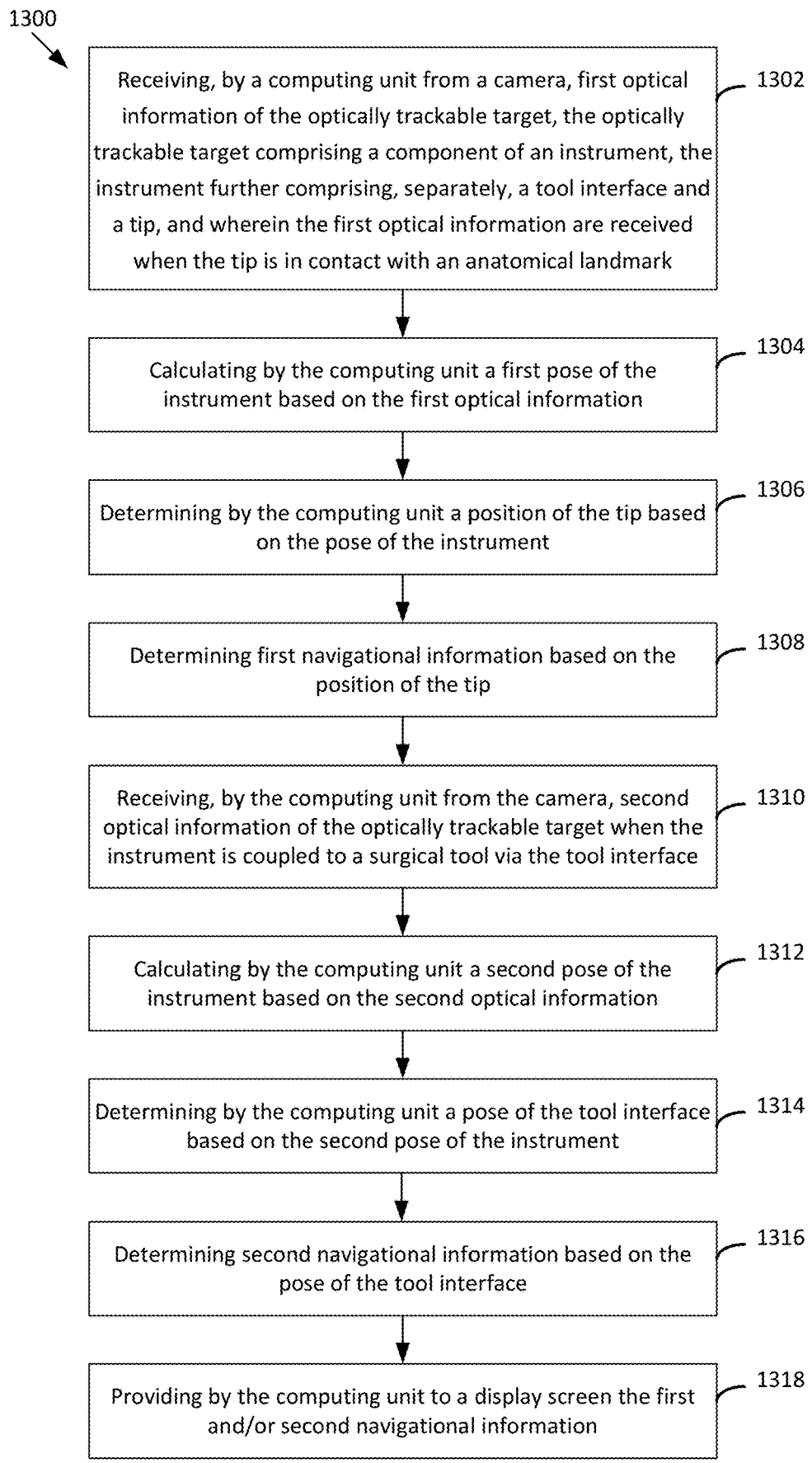
FIG. 13 is a flowchart showing a computer implemented method to perform a navigated surgical procedure according to an example.

FIG. 13 is a flowchart showing a computer implemented method 1300 to perform a navigated surgical procedure. The method 1300 comprises, at step 1302: receiving, by a computing unit from a camera, first optical information of the optically trackable target, the optically trackable target comprising a component of an instrument, the instrument further comprising, separately, a tool interface and a tip, and wherein the first optical information are received when the tip is in contact with an anatomical landmark. At step 1304, the method 1300 comprises calculating by the computing unit a first pose of the instrument based on the first optical information and, at step 1306, determining by the computing unit a position of the tip based on the pose of the instrument. At step 1308, the method 1300 comprises determining first navigational information based on the position of the tip. At step 1310, the method comprises receiving, by the computing unit from the camera, second optical information of the optically trackable target when the instrument is coupled to a surgical tool via the tool interface, and, at step 1312, calculating by the computing unit a second pose of the instrument based on the second optical information. There is determined, by the computing unit, a pose of the tool interface based on the second pose of the instrument at step 1314; and, at step 1316, second navigational information based on the pose of the tool interface. At step 1318 the method 1300 comprises providing by the computing unit to a display screen the first and/or second navigational information.

In method 1300, the first and/or second navigational information may be provided to the display screen by the computing unit based on navigation context information. It will be understood that first navigational information may be determined and provided before any second navigational information is determined and/or provided and vice versa. The reference to "first" and "second" is disambiguate the navigation information and not a reference to an order of operations. The reference to receiving optical information from the camera should not be limited to only receiving a single instance of such information. For example, first optical information may be received at one instance in time and used to determine the first navigational information based on the position of the tip at that instance in time. Some optical information may be received at a second instance of time and used to determine the second navigational information. Again, the first and second instances do not require an order of occurrence in real time.

The computing unit described herein may comprise a laptop, workstation or other computer having one or more processors (e.g. microprocessors), storage devices (e.g. RAM, ROM or other memory device, removable devices), communication devices, buses, input devices, output devices and/or I/O devices such as keyboard, buttons, foot pedal, pointing device, microphone, speaker, lights, bell, display screen (which may be touch or gesture enabled), etc. and these may be on-board or coupled thereto via communication interfaces and/or buses. Communication interfaces and communication devices may couple the computing unit in a wired or wireless manner to one or more networks or to input, output and/or I/O devices. Software (e.g. instructions stored in memory) may provide components for configuring the computing unit when the software is executed by the one or more processors. The various clinical applications and tracking modalities referred to in this description are meant to be exemplary and non-limiting.

What is claimed is:

1. A system to provide navigational information during a surgery comprising:
    an instrument comprising:
        a tip;
        a tool interface, separate from the tip, the tool interface for coupling to a separate surgical tool; and
        an optically trackable target;
    a computing unit comprising a processor and a storage device storing instructions which when executed by the processor configure the computing unit to:
        receive from a camera optical information of the optically trackable target;
        calculate a pose of the instrument based on the optical information;
        determine a position of the tip based on the pose of the instrument;
        determine first navigational information based on the position of the tip;
        determine a pose of the tool interface based on the pose of the instrument;
        determine second navigational information based on the pose of the tool interface; and
        provide at least one of the first and second navigational information to one or more of: a display unit for displaying to a user, computer memory for storage, and a robotic control system.

2. The system of claim 1 wherein the instrument has two opposite ends, and the tip is on one end, the tool interface is on the other end, and the optically trackable target is between the two ends.

3. The system of claim 1 wherein the computing unit is further configured to determine navigation context information; and provide the at least one of the first and second navigational information based on the navigation context information.

4. The system of claim 3 wherein the computing unit determines the navigation context information based, at least in part, on the pose of the instrument.

5. The system of claim 3 wherein the computing unit is configured to execute a software workflow comprising a series of steps, and determine the navigation context information, at least in part, based on a current step in the software workflow.

6. The system of claim 1, wherein the tool interface comprises a planar feature.

7. The system of claim 6 wherein the planar feature comprises a magnet, and is configured to mate with a cutting slot of a cutting guide.

8. The system of claim 1 wherein the computing unit is further configured to determine at least one of the position of the tip and the pose of the tool interface based at least in part on calibration data.

9. The system of claim 8 wherein the calibration data is stored in memory accessible to the computing unit, and derived from manufacturing specifications of the instrument.

10. The system of claim 8 wherein the calibration data is determined based on a calibration routine.

11. The system of claim 1 wherein the first navigational information is limb position change and the second navigational information is implant alignment.

12. The system of claim 11 wherein the surgery is a hip arthroplasty and wherein the computing unit is configured to execute a software workflow comprising a series of steps to provide assistance for performing the surgery.

13. The system of claim 1 wherein the instrument is pre-sterilized, single-use and disposable.

14. The system of claim 1 wherein the first navigational information defines at least one anatomical axis of a bone and the second navigational information is the alignment of a bone cutting guide relative to the at least one anatomical axis.

15. The system of claim 14 wherein the surgery is a knee arthroplasty and wherein the computing unit is configured to execute a software workflow comprising a series of steps to provide assistance for performing the surgery.

16. The system of claim 6, wherein the planar feature is without a magnet, and the planar feature is configured to mate with a cutting slot of a cutting guide.

17. The system of claim 1, wherein the second navigational information relates to the surgical tool when the surgical tool is coupled to the tool interface.

18. The system of claim 4, wherein the computing device determines an orientation of the instrument to identify whether the tip or the tool interface is relevant in the context of the surgery to determine which of the first navigational information and second navigational information is determined.

19. A computer implemented method to perform a navigated surgical procedure comprising:
   receiving, by a computing unit from a camera, the computing unit comprising a processor, first optical information of an optically trackable target, the optically trackable target comprising a component of an instrument, the instrument further comprising, separately, a tool interface and a tip, the tool interface for coupling to a separate surgical tool, and wherein the first optical information is received when the tip is in contact with an anatomical landmark;
   calculating, by the processor, a first pose of the instrument based on the first optical information;
   determining, by the processor, a position of the tip based on the first pose of the instrument;
   determining, by the processor, first navigational information based on the position of the tip;
   receiving, by the processor, from the camera, second optical information of the optically trackable target when the instrument is coupled to a surgical tool via the tool interface;
   calculating, by the processor, a second pose of the instrument based on the second optical information;
   determining, by the processor, a pose of the tool interface based on the second pose of the instrument;
   determining, by the processor, second navigational information based on the pose of the tool interface; and
   providing, by the processor, to a display screen the first and/or second navigational information.

20. The method of claim 19 wherein the first and/or second navigational information is provided to the display screen by the computing unit based on navigation context information.

21. The method of claim 19 wherein the tip and the tool interface are at opposite ends of the instrument.

* * * * *